US00PP21829P2

(12) United States Plant Patent

Gomez Bullis

(10) Patent No.: US PP21,829 P2

(45) Date of Patent: Mar. 29, 2011

(54) *NEOREGELIA* PLANT NAMED 'GREEN APPLES'

(50) Latin Name: ***Neoregelia macrosepala*×*Neoregelia carolinae***

Varietal Denomination: Green Apples

(75) Inventor: Patricia E. Gomez Bullis, Princeton, FL (US)

(73) Assignee: Bullis Bromelinds, Princeton, FL (US)

( * ) Notice: Subject to any disclaimer, the term of this patent is extended or adjusted under 35 U.S.C. 154(b) by 0 days.

(21) Appl. No.: 12/462,570

(22) Filed: Aug. 5, 2009

(51) Int. Cl.
*A01H 5/00* (2006.01)

(52) U.S. Cl. ..... Plt./370

(58) Field of Classification Search ..... Plt./370
See application file for complete search history.

(56) References Cited

PUBLICATIONS

FCBS Bromeliad Phot Index Database for *Neoregelia* 'Green Apple' retrieved on Jul. 28, 2010. Retrieved from the Internet at <http:web.archive.org/web/*/http://fcbs.org/pictures/Neo.htm> Feb. 16, 2001, 2 pages.*

* cited by examiner

*Primary Examiner*—June Hwu
(74) *Attorney, Agent, or Firm*—C. A. Whealy

(57) ABSTRACT

A new and distinct cultivar of *Neoregelia* plant named 'Green Apples', characterized by its upright and outwardly arching growth habit; leaves of vegetative plants are green and red purple bi-colored becoming red purple with development; and good interiorscape and landscape performance.

2 Drawing Sheets

Botanical designation: *Neoregelia macrosepala*×*Neoregelia carolinae.*

Cultivar denomination: 'GREEN APPLES'.

BACKGROUND OF THE INVENTION

The present invention relates to a new and distinct cultivar of *Neoregelia* plant, botanically known as *Neoregelia macrosepala*×*Neoregelia carolinae* and hereinafter referred to by the name 'Green Apples'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of an unnamed proprietary selection of *Neoregelia macrosepala,* not patented, as the female, or seed, parent with the *Neoregelia carolinae* 'Meyendorffii', not patented, as the male, or pollen, parent. The new *Neoregelia* plant was discovered and selected by the Inventor as a single plant within the progeny of the stated cross-pollination in a controlled greenhouse environment in Princeton, Fla. in 2002.

Asexual reproduction of the new *Neoregelia* plant by offsets in a controlled environment in Princeton, Fla. since 2002, has shown that the unique features of this new *Neoregelia* plant are stable and reproduced true to type in successive generations.

SUMMARY OF THE INVENTION

Plants of the new *Neoregelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Green Apples'. These characteristics in combination distinguish 'Green Apples' as a new and distinct cultivar of *Neoregelia:*

1. Upright and outwardly arching growth habit.
2. Leaves of vegetative plants are green and red purple bi-colored becoming red purple with development.
3. Good interiorscape and landscape performance.

Plants of the new *Neoregelia* differ from plants of the female parent selection in the following characteristics:

1. Plants of the new *Neoregelia* have fewer whorls of leaves than plants of the female parent selection.
2. Leaves of plants of the new *Neoregelia* are shorter and broader than leaves of plants of the female parent selection.
3. Leaves of plants of the new *Neoregelia* are green and red purple bi-colored whereas leaves of plants of the female parent selection are green and pink bi-colored.
4. Leaves of plants of the new *Neoregelia* develop their predominant red purple coloration earlier than leaves of plants of the female parent selection develop their pink coloration.

Plants of the new *Neoregelia* differ from plants of the male parent, 'Meyendorffii', in the following characteristics:

1. Plants of the new *Neoregelia* are taller and broader than plants of 'Meyendorffii'.
2. Leaves of plants of the new *Neoregelia* develop their predominant red purple coloration earlier than leaves of plants of 'Meyendorffii'.

Plants of the new *Neoregelia* can be compared to plants of the *Neoregelia hybrida* 'Tangerine', not patented. Plants of the new *Neoregelia* and 'Tangerine' differ primarily in leaf color and leaf pattern.

Plants of the new *Neoregelia* can also be compared to plants of the *Neoregelia* 'Green Apple', not patented. Plants of the new *Neoregelia* and 'Green Apple' differ primarily in leaf color as leaves of plants of the new *Neoregelia* develop their predominant red purple coloration earlier than leaves of plants of 'Green Apple'. In addition, the leaf color patterns of plants of the new *Neoregelia* are different than leaf color patterns of plants of 'Green Apple'.

BRIEF DESCRIPTION OF THE PHOTOGRAPHS

The accompanying colored photographs illustrate the overall appearance of the new *Neoregelia* plant, showing the colors as true as it is reasonably possible to obtain in colored reproductions of this type. Colors in the photographs may differ slightly from the color values cited in the detailed botanical description which accurately describe the colors of the new *Neoregelia*.

The photograph at the bottom of the first sheet is a side perspective view of a typical vegetative plant of 'Green Apples' grown in a container.

The photograph at the top of the first sheet is a top perspective view of a typical vegetative plant of 'Green Apples'.

The photograph at the bottom of the second sheet is a side perspective view of a typical flowering plant of 'Green Apples' grown in a container.

The photograph at the top of the second sheet is a top perspective view of a typical flowering plant of 'Green Apples'.

DETAILED BOTANICAL DESCRIPTION

The aforementioned photographs and following observations, measurements and values describe plants grown in 15-cm containers in Princeton, Fla. during the spring under commercial practice in a polypropylene-covered shade house with day temperatures ranging from 10° C. to 32° C., night temperatures ranging from 7° C. to 29° C. and light levels averaging 3,200 foot-candles. Single plants used for the photographs and description were 18 months old. In the following description, color references are made to The Royal Horticultural Society Colour Chart, 2007 Edition, except where general terms of ordinary dictionary significance are used.

Botanical classification: *Neoregelia macrosepala*×*Neoregelia carolinae* 'Green Apples'.

Parentage:

*Female, or seed, parent.*—Unnamed proprietary selection of *Neoregelia macrosepala,* not patented.

*Male, or pollen, parent.*—*Neoregelia carolinae* 'Meyendorffii', not patented.

Propagation:

*Type.*—By offsets.

*Time to initiate roots, summer.*—About 30 days at 30° C. to 32° C.

*Time to initiate roots, winter.*—About 45 days at 30° C. to 32° C.

*Time to produce a rooted young plant, summer.*—About three to four months at 30° C. to 32° C.

*Time to produce a rooted young plant, winter.*—About three to four months at 18° C. to 22° C.

*Root description.*—Medium in thickness, fibrous; yellow to tan in color.

*Rooting habit.*—Moderately freely branching; medium density.

Plant description:

*Plant form/growth habit.*—Upright and outwardly arching growth habit; rosette leaves are erect when young, becoming outwardly arching with development; plants readily produce uniform offsets; vigorous growth habit.

*Plant height, vegetative plants.*—About 27 cm.

*Plant height, flowering plants.*—About 16 cm.

*Plant diameter or spread, vegetative plants.*—About 46 cm.

*Plant diameter or spread, flowering plants.*—About 41 cm.

*Internode length, vegetative and flowering plants.*—About 3.5 mm.

Foliage description:

*Arrangement.*—Rosette, spiral phyllotaxis; simple; sessile, clasping.

*Shape.*—Oblong to broadly ensiform.

*Apex.*—Cuspidate.

*Base.*—Truncate.

*Margin.*—Serrate, spinose.

*Length.*—About 31 cm.

*Width.*—About 6.3 cm.

*Texture.*—Smooth, glabrous; leathery.

*Venation pattern.*—Parallel.

*Color.*—Developing leaves, vegetative plants, upper surface: Close to 146B; towards the apex, slightly tinted with close to 60A. Developing leaves, vegetative plants, lower surface: Close to 146B to 146C. Developed leaves, vegetative plants, upper surface: Close to 146A tinted with close to 59B; towards the apex, overlain with close to 60A; towards the base, close to 145A to 145B; venation, close to 146A. Developed leaves, vegetative plants, lower surface: Towards the base, close to 146B; center and towards the apex, close to 146C tinted with close to 60B to 60C; venation, close to 146C. Upper leaves, flowering plants, upper surface: Towards the apex, close to 187B; centers, close to 59B; towards the base, close to 157B to 157C; venation, close to 145A. Upper leaves, flowering plants, lower surface: Towards the apex, close to 187B; centers, close to 59B; towards the base, close to 157B to 157C; longitudinal streaks, close to 146B; venation, close to 146C.

Inflorescence description:

*Inflorescence form.*—Terminal flat-topped compact corymb located inside the leaf rosette; about 88 flowers develop per inflorescence.

*Flower longevity.*—Individual flowers last about one to two days on the plant; flowers persistent.

*Inflorescence length.*—About 5.5 cm.

*Inflorescence diameter.*—About 4 cm.

*Flower size.*—Length: About 4 cm. Diameter: About 7 mm.

*Fragrance.*—None detected.

*Flower buds.*—Length: About 2.8 cm. Diameter: About 4 mm. Shape: Elongated oblong. Color: Close to N88A.

*Petals.*—Quantity per flower: Three in a single whorl. Shape: Oblanceolate. Apex: Mucronate. Base: Truncate. Margin: Entire. Length: About 2.8 cm. Width: About 4 mm. Texture: Smooth, glabrous. Color: When opening, upper surface: Close to 83A. When opening, lower surface: Close to N88A. Fully opened, upper surface: Towards the apex, close to 83A; center, close to N88B; towards the base, close to NN155D. Fully opened, lower surface: Towards the apex, close to N88A; towards the base, close to NN155D.

*Flower bracts.*—Quantity per flower: One. Shape: Oblanceolate. Length: About 3.4 cm. Width: About 9 mm. Texture: Membraneous. Color: Towards the apex, close to 146D; towards the base, close to N157D.

*Sepals.*—Quantity per flower: Three in a single whorl. Shape: Lanceolate. Apex: Acuminate. Base: Truncate. Margin: Entire. Length: About 2.4 cm. Width: About 7 mm. Texture: Smooth, glabrous. Color, upper surface: Towards the apex, close to 146D; towards the base, close to 145D. Color, lower surface: Towards the apex, close to 145A; towards the base, close to 157D.

*Peduncles.*—Strength: Strong. Aspect: Typically erect. Length: About 4.2 cm. Diameter: About 1.2 cm. Texture: Smooth, glabrous. Color: Close to 155A.

*Pedicels.*—Strength: Strong. Aspect: Typically erect to somewhat outward. Length: About 5 mm. Diameter: About 2.5 mm. Texture: Smooth, glabrous. Color: Close to 155D.

*Stamens.*—Quantity per flower: About six. Filament length: About 1.2 cm. Filament color: Close to NN155D. Anther shape: Lanceolate. Anther length: About 5 mm. Anther color: Close to 158C. Pollen amount: Scarce. Pollen color: Close to 155A.

*Pistils.*—Quantity per flower: One. Pistil length: About 3.2 cm. Stigma shape: Rounded. Stigma color: Close to NN155B. Style length: About 1.8 cm. Style color: Close to NN155C. Ovary color: Close to NN155C.

*Seed/fruit.*—Seed and fruit production have not been observed.

Temperature tolerance: Plants of the new *Neoregelia* have been observed to tolerate temperatures ranging from about 4° C. to about 37° C.

Interior & garden performance: Plants of the new *Neoregelia* have been observed to have good postproduction longevity under interior conditions and to have good garden performance.

Disease/pest resistance: Resistance to pathogens and pests common to *Neoregelia* has not been observed.

It is claimed:

1. A new and distinct *Neoregelia* plant named 'Green Apples' as illustrated and described.

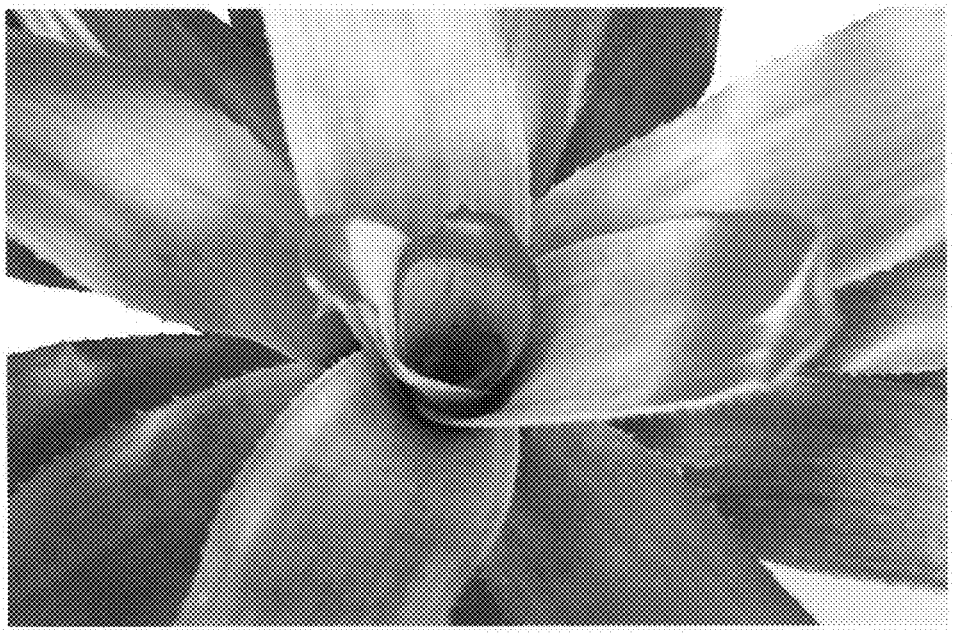
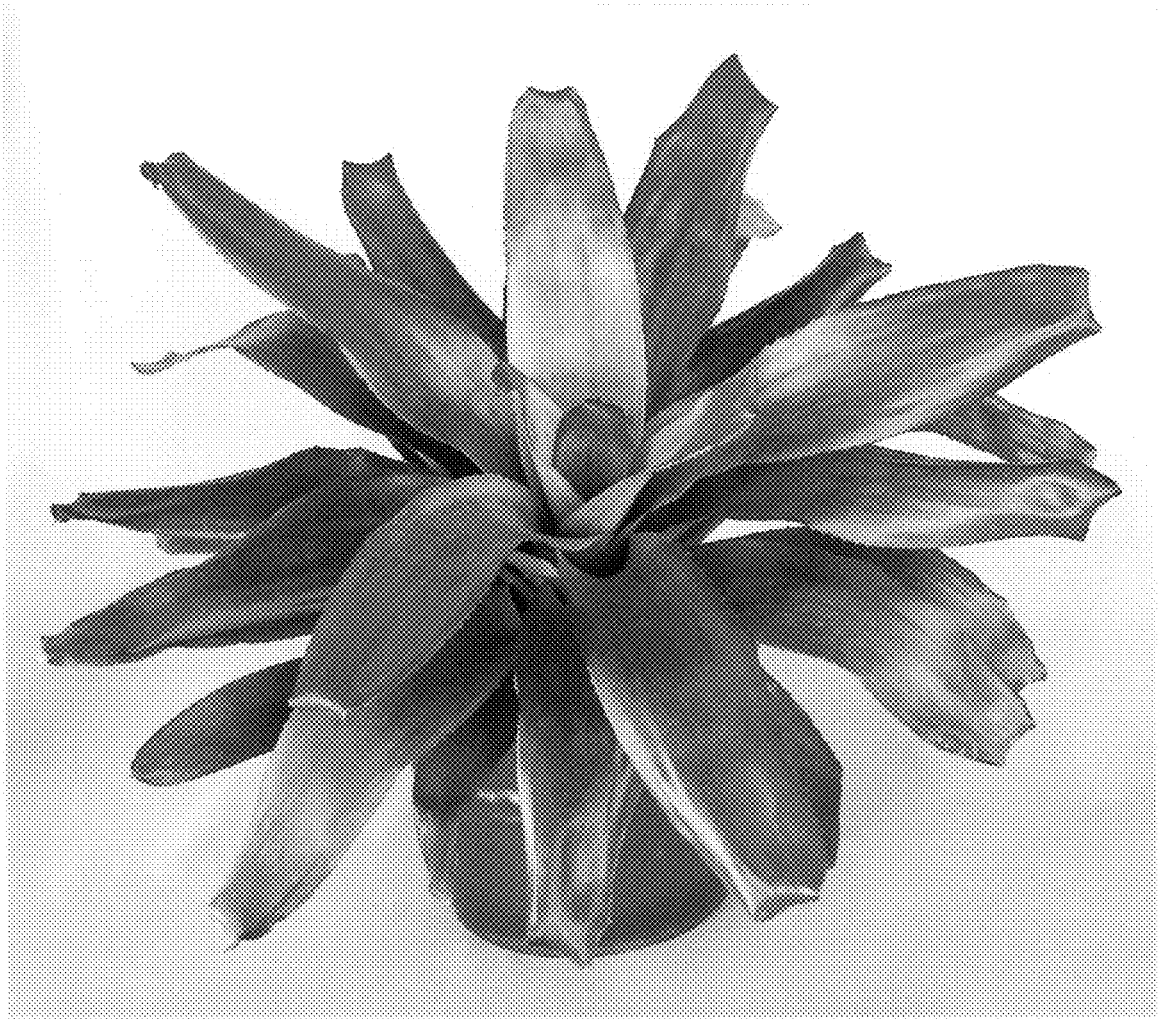

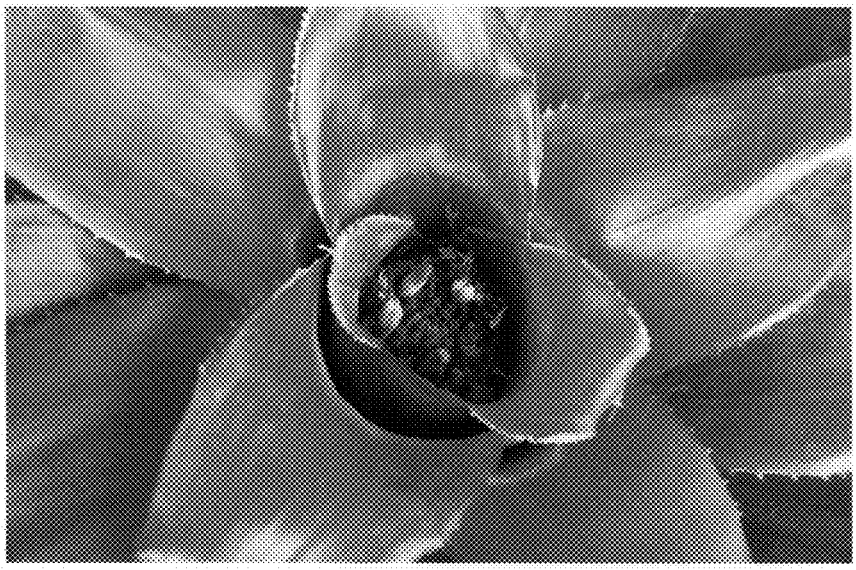
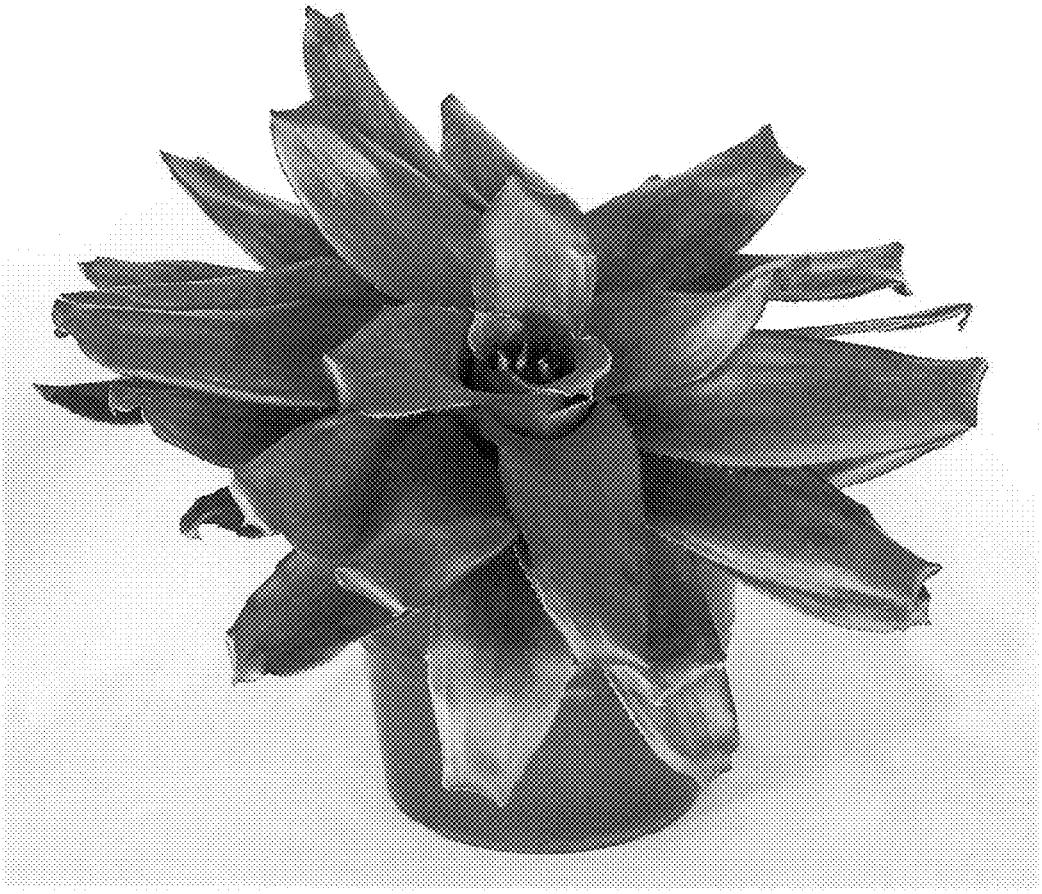

* * * * *